United States Patent [19]

Schleppinghoff

[11] 4,377,393
[45] Mar. 22, 1983

[54] PROCESS FOR THE PREPARATION OF A MIXTURE CONSISTING ESSENTIALLY OF ISO-BUTENE OLIGOMERS AND METHYL TERT.-BUTYL ETHER, ITS USE, AND FUELS CONTAINING SUCH MIXTURE

[75] Inventor: Bernhard Schleppinghoff, Dormagen, Fed. Rep. of Germany

[73] Assignee: EC Erdolchemie GmbH, Cologne, Fed. Rep. of Germany

[21] Appl. No.: 200,700

[22] Filed: Oct. 27, 1980

[30] Foreign Application Priority Data

Nov. 3, 1979 [DE] Fed. Rep. of Germany ....... 2944457

[51] Int. Cl.³ .............................................. C10L 1/18
[52] U.S. Cl. ......................................... 44/53; 44/56; 568/697
[58] Field of Search ..................... 44/53, 56; 568/697

[56] References Cited

U.S. PATENT DOCUMENTS

| | | | |
|---|---|---|---|
| 2,255,275 | 9/1941 | Stahly .................................. | 568/697 |
| 2,384,796 | 9/1945 | Carmody et al. ........................ | 44/53 |
| 2,480,940 | 9/1949 | Leum et al. ........................ | 260/614 |
| 3,482,952 | 12/1969 | Sieg et al. ............................ | 568/697 |
| 4,039,590 | 8/1977 | Ancillotti et al. ................... | 568/697 |
| 4,182,913 | 1/1980 | Takezono et al. ....................... | 44/56 |

FOREIGN PATENT DOCUMENTS 1213837  4/1966  Fed. Rep. of Germany .
907429  10/1962  United Kingdom .

*Primary Examiner*—Jacqueline V. Howard
*Attorney, Agent, or Firm*—Sprung, Horn, Kramer & Woods

[57] ABSTRACT

A fuel for a carburetor type engine consisting essentially of isobutene oligomers and methyl tert.-butyl ether, said fuel prepared by a process comprising:

(a) in a first step contacting a mixture of straight chain and branched butanes and butenes with an acid catalyst whereby to oligomerize 50% to 90% by weight of the isobutene contained therein:

(b) contacting the reaction mixture from step (a) with at least a molar amount of methanol, relative to the residual isobutene, in the presence of an acid catalyst; and (c) separating off from the reaction mixture unreacted butanes and butenes.

11 Claims, 1 Drawing Figure

PROCESS FOR THE PREPARATION OF A MIXTURE CONSISTING ESSENTIALLY OF ISO-BUTENE OLIGOMERS AND METHYL TERT.-BUTYL ETHER, ITS USE, AND FUELS CONTAINING SUCH MIXTURE

The present invention relates to a process for the preparation, from $C_4$ cuts containing isobutene, of a mixture which consists essentially of iso-butene oligomers and methyl tert.-butyl ether, the use of such a mixture as a fuel or as an additive to a fuel with a high octane number, and fuels, for carburetor-type engines, which have a high octane number and contain such a mixture.

Thermal and catalytic cracking of mineral oil fractions, for example light petroleum mixtures, and dehydrogenation of n- and iso-butane gives, after the removal of butadiene, $C_4$ cuts which contain, in addition to n- and iso-butane and n-butenes, relatively large amounts of iso-butene. This iso-butene can be put to diverse uses and is used, inter alia, as a starting material for the preparation of alkylation gasolines, di- and triisobutene (DIB and TIB) and methyl tert.-butyl ether (MTBE). These products, in addition to others, are of great importance as agents for improving the octane number of engine fuels. The preparation of these substances is usually effected on acid catalysts, such as sulphuric acid, phosphoric acid or anhydrides thereof, or on acid ion exchangers, and has been known for a long time.

Thus, when a $C_4$ cut is heated to 85° to 140° C. with 50 to 70% strength by weight sulphuric acid, the main product is diisobutene (U.S. Pat. No. 2,237,292).

The main product is likewise diisobutene when iso-butene is treated, in iso-butane, with phosphorus pentoxide at 0° C., triisobutene being preferentially formed at a higher temperature (U.S. Pat. No. 2,409,727).

More recent processes describe the conversion of iso-butene into diisobutene without the use of sulphuric acid, for example in the presence of acid ion exchangers, it being possible to carry out the reaction in several circulatory reactors connected in series or in a tube reactor (Hydrocarbon Proc., Volume 52 (4), 171 (1973)).

However, the processes known hitherto for the production of diisobutene and triisobutene have the disadvantage that they give rise to serious corrosion and waste disposal problems when acids and anhydrides thereof are used, and problems arise during removal of the catalyst when, for example, ion exchangers are used in circulatory reactors. In addition, in the case of substantial conversion of the i-butene, the long residence time in the circulatory reactors or tube reactors leads to the undesired formation of higher oligomers and to marked isomerization of the valuable 1-butene into 2-butene.

If iso-butene or a $C_4$ cut containing iso-butene is reacted with methanol on an acid ion exchanger, methyl tert.-butyl ether is obtained. In order to achieve a good selectivity for the reaction, methanol is added in excess. After the reaction, the unreacted $C_4$ hydrocarbons, the unreacted methanol and the ether formed are separated from one another in a distillation step (Hydrocarbon Proc., Volume 56 (11), 185 (1977)).

A single product is indeed obtained in this process, but if the MTBE is to be used as a mixing component for a fuel for carburetor-type engines, it is necessary to admix higher-boiling components, such as reformed cuts containing aromatics, as a result of the low boiling point of MTBE. It is also known to first subject $C_4$ mixtures to etherification with methanol, the predominant proportion of the iso-butene being converted into methyl tert.-butyl ether, and to subject the residue to an alkylation reaction, in order thus to obtain a high-octane MTBE/$C_8$ hydrocarbon mixture (DE-OS (German Published Specification) No. 2,246,004). The process mentioned for the preparation of a mixture of MTBE and $C_8$ hydrocarbons for direct use as a fuel for carburetor-type engines has the following disadvantages: after the etherification, the $C_4$ hydrocarbons, the MTBE and the higher hydrocarbons must be carefully separated. Furthermore, the $C_4$ hydrocarbons which remain must be freed from methanol, before the alkylation, by washing with water. Excess methanol must likewise be separated off from the MTBE by washing with water. Moreover, the alkylation reaction in the process mentioned is carried out in the presence of sulphuric acid, which gives rise to the known disposal problems for removing the waste sulphuric acid and the known corrosion problems.

A process has now been found for the preparation of a mixture consisting essentially of iso-butene oligomers and methyl tert.-butyl ether, that is characterized in that (a) a mixture of straight-chain and branched butanes and butenes are reacted on an acid catalyst in a manner such that 50 to 90% by weight of the iso-butene contained in the mixture is converted into iso-butene oligomers, (b) the reaction mixture thus obtained is then reacted with at least a molar amount of methanol, relative to the residual iso-butene, on an acid catalyst and (c) the unreacted butanes and butenes are separated off from the reaction mixture.

An example of a mixture of straight-chain and branched butanes and butenes for the process according to the invention is a $C_4$ cut such as is obtained, for example, on thermal or catalytic cracking of mineral oil fractions, after the butadiene contained therein has been removed. The typical composition of such $C_4$ cuts is given in the following table:

|          | Steam Cracker    | Catalytic Cracker  |
|----------|------------------|--------------------|
| n-Butane | 6–8% by weight   | about 10% by weight |
| i-Butane | 2–3% by weight   | about 34% by weight |
| i-Butene | 44–49% by weight | about 15% by weight |
| 1-Butene | 24–28% by weight | about 13% by weight |
| 2-Butene | 19–21% by weight | about 28% by weight |

Examples which may be mentioned of acid catalysts for stages (a) and (b) of the process according to the invention are strong mineral acids and anhydrides thereof, such as sulphuric acid, phosphoric acid, sulphur trioxide, oleum or phosphorus pentoxide, and strongly acid ion exchangers.

Examples of strongly acid ion exchangers which may be mentioned are formaldehyde/phenol resins containing sulphonic acid groups or polystyrenes which contain sulphonic acid groups and are crosslinked with divinylbenzene.

It is possible to carry out stages (a) and (b) of the process according to the invention in the presence of the same acid catalyst or in the presence of different acid catalysts.

Strongly acid ion exchangers are preferably employed for the process according to the invention, and polystyrene which contains sulphonic acid groups and is crosslinked with divinylbenzene is particularly preferred.

The volumetric hourly space velocity is given, in liters of $C_4$ hydrocarbon employed per liter of acid catalyst per hour, as the concentration of the acid catalyst for stages (a) and (b) of the process according to the invention. Values of 0.05 to 50, preferably of 0.2 to 15, may be mentioned as examples. The acid catalyst can have the same concentration or different concentrations in stages (a) and (b).

In stage (a) of the process according to the invention, the amount of iso-butene contained in the starting material which is converted into oligomers is, for example, 50 to 90% by weight, preferably 70 to 80% by weight.

In stage (b) of the process according to the invention, at least a molar amount of methanol, relative to the residual iso-butene, is employed in order to achieve as substantial a conversion as possible of the iso-butene. The amount of methanol employed is preferably 1 to 2 mols, and particularly preferably 1.2 to 1.5 mols, relative to the residual iso-butene.

The temperature range from 20° to 120° C., preferably from 25° to 70° C., may be mentioned as a temperature for stage (a) of the process according to the invention.

In addition, in the process according to the invention, the isomerization of the n-butene-1 into n-butene-2 is substantially suppressed within this temperature range.

A temperature range from 25° to 90° C., preferably from 45° to 75° C., may be mentioned as an example of the temperature for stage (b) of the process according to the invention.

The pressure for stages (a) and (b) is chosen such that the substances participating in the process according to the invention are present in liquid form. A general pressure range which may be mentioned is that from 2 to 30 bars. The pressure of course depends, in the manner known to the expert, on the reaction procedure of the process according to the invention.

In stage (c) of the process according to the invention, the reaction product is first let down and then passes into a separation apparatus, known to the expert as a debutanizer, in which all the $C_4$ hydrocarbons are removed as the top product. This top product has an iso-butene content of less than 1% by weight. The bottom product has a content of $C_4$ hydrocarbons of less than 1% and a methanol content of less than 5%. It can be employed, for example, as a high-octane finished fuel mixture for carburetor-type engines or as an additive for improving the octane number of fuels for carburettor-type engines. The mixture prepared according to the invention has the following composition and the following properties.

| Composition and properties of the bottom product | |
|---|---|
| $C_4$ hydrocarbons | 1% by weight |
| $C_8$ hydrocarbons | 40–60% by weight |
| $C_{12}$ hydrocarbons | 15–20% by weight |
| $C_{16}$ hydrocarbons | 1–3% by weight |
| MTBE | 10–30% by weight |
| Methanol | 0.1–4% by weight |
| Bromine number (g of $Br_2$/100 ml) | 100 |
| Start of boiling | 40° C. |
| 50% | 110° C. |
| End of boiling | 200° C. |
| Vapour pressure according to Reid | 0.8 Kp/cm² at 38° C. |
| RON* clear | 101–103 |
| RON 0.15 TEL/1*** | 102–103 |

| -continued | | |
|---|---|---|
| Composition and properties of the bottom product | | |
| EON** | clear | 83–86 |
| EON | 0.15 TEL/1*** | 85–88 |

*Research (test) octane number,
**Engine octane number,
***Tetraethyl-lead.

It can be desirable to decrease the olefin content of the product by partial hydrogenation. After hydrogenation of about 50% of the olefins, the following engine data are obtained:

| RON | clear | 101–103 |
|---|---|---|
| RON | 0.15 TEL | 102–105 |
| EON | clear | 85–88 |
| EON | 0.15 TEL | 88–91 |

The bromine number of the partially hydrogenated product is about 40.

Stages (a) and (b) of the process according to the invention can be carried out in a combined apparatus or in 2 separate apparatuses. If liquid acid catalysts are used, the starting material in general passes through the apparatuses from the bottom upward, so that the hydrocarbon mixture, which has a lower specific gravity, flows through the catalyst, which has the higher specific gravity. In the case of the preferred use of solid acid catalysts, for example strongly acid ion exchangers, the starting material can pass through the apparatuses either from the bottom upward or from the top downward. To achieve good distribution of the starting material over the entire cross-section of the reactor and to obtain optimum contact with the acid catalyst, the apparatuses can be provided with built-in fitments known to the expert, such as nozzles or perforated plates for the entry of the starting material, and trays and baffles over the entire length of the reactor. The reactor can also be in the form of a tube reactor.

If a combined reactor is used for stages (a) and (b) of the process according to the invention, the starting mixture is introduced into the reactor from the bottom or from the top, depending on the nature of the acid catalyst employed. At a suitable point in the combined reactor, at which, when viewed in the direction of flow of the reaction mixture, 50 to 90% by weight of the iso-butene present in the starting material have been converted into iso-butene oligomers, the amount of methanol described above is fed in and the reaction is brought to completion with stage (b) of the process according to the invention.

In another process variant, stages (a) and (b) of the process according to the invention are carried out in separate reaction apparatuses. The reaction apparatuses for the two stages of the process can be different, for example in the form of a tube reactor or in the form of a fixed bed reactor. Furthermore, the same acid catalyst or different acid catalysts, from those mentioned above, can be used in the reactors for the two stages.

BRIEF DESCRIPTION OF DRAWING

Such a process variant will be described with the aid of the accompanying drawing which is a flow diagram.

DESCRIPTION OF SPECIFIC EMBODIMENT

Figure 1:
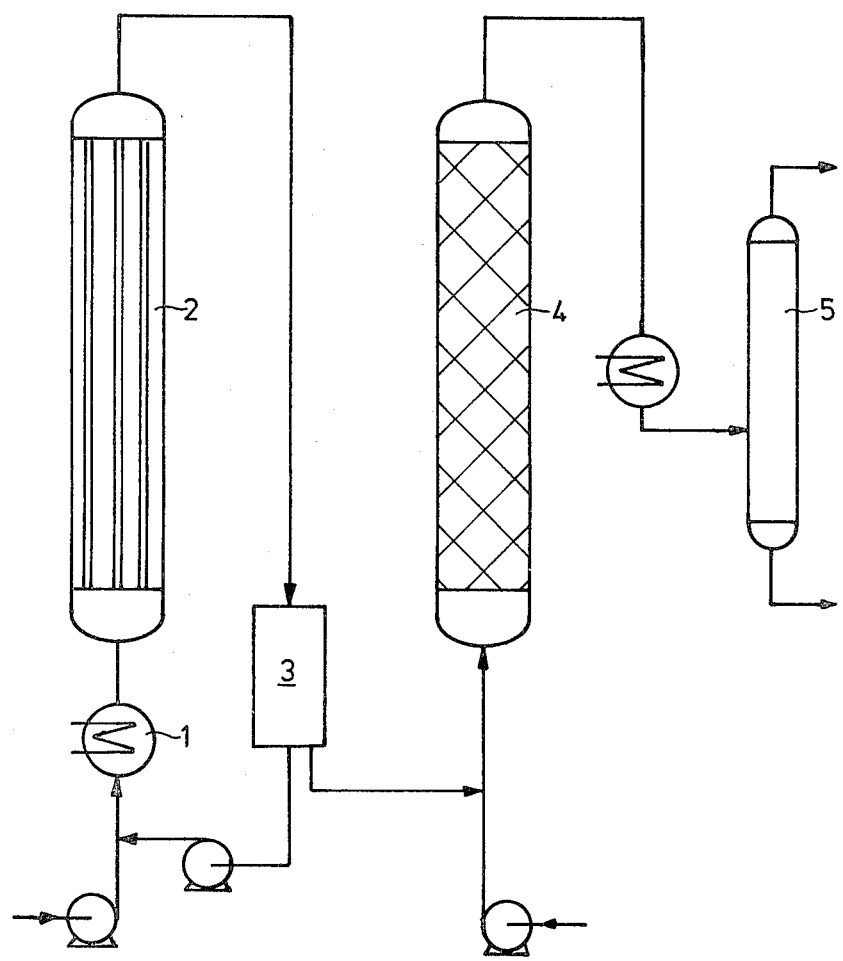

The $C_4$ mixture containing iso-butene is introduced, via a pre-heater (1) into a fixed bed tube reactor (2) with the aid of a pump. The reactor (2) consists of a cooled system of tubes filled with the chosen catalyst, in which a suitable cooling liquid can pass through the free space around the tubes in order to remove the heat of the exothermic reaction. The pump maintains a pressure such that the reaction mixture remains liquid. The reaction mixture is first passed from the reactor (2) into an intermediate vessel (3), from where part of the reaction mixture can be recycled, as a circulating stream, into the reactor (2). The remaining portion of the mixture from the intermediate vessel (3) is passed into a fixed bed reactor (4), and before its entry into this reactor, methanol is added in the amount required according to the invention. The reactor (4) is also operated under a pressure such that the reaction mixture remains liquid. After leaving the reactor (4), the reaction mixture is introduced into a separation apparatus (debutanizer (5) and is separated into the fuel mixture prepared according to the invention, as the bottom product, and the $C_4$ raffinate as the top product.

A mixture of diisobutene, triisobutene, tetraisobutene and methyl tert.-butyl ether which contains only a minor proportion of $C_4$ hydrocarbons and which, if appropriate after complete or partial hydrogenation of the olefinic constituents, can be used both as a finished motor fuel and as an additive for increasing the octane number of other motor fuels, can be prepared in the process according to the invention.

The invention thus relates to the use of the mixture prepared according to the invention as a fuel or as an additive to a fuel for carburetor-type engines.

The invention furthermore relates to fuels, for carburetor-type engines, which contain the mixture prepared according to the invention.

It is, of course, also possible to separate the mixture which can be prepared in the process according to the invention into the individual pure components and to use these separately as additives to motor fuels or as solvents.

The oligomerization of iso-butene in the process according to the invention leads mainly to 2,4,4-trimethyl-1-pentene, the high octane number of which is known.

The proportion of $C_8$, $C_{12}$ and $C_{16}$ oligomers can be adapted to the requirements for motor fuel by the circulatory procedure and by adjusting the temperature of the oligomerization in stage (a) of the process according to the invention. It is not necessary for the $C_4$ hydrocarbon stream obtained in the subsequent separation in the process according to the invention to be recycled, as is described in other processes, since the iso-butene is selectively converted virtually completely. This $C_4$ stream obtained from the separation stage of the according to the invention contains about 25 to 40% by weight of valuable n-butene-1.

In stage (b) of the process according to the invention, the unreacted iso-butene is reacted with methanol to the extent that the end product contains about 5 to about 40% by weight of methyl tert.-butyl ether, depending on the procedure of this stage. Since this ether is known to have a test octane number of 117, the oligomer, which already has a high octane number, is improved further.

Surprisingly, the formation of dimethyl-hexenes for example from iso-butene and n-butenes, with a low test octane number of about 93 is largely suppressed.

In contrast to processes of the state of the art, which require long residence times for substantial conversion of the i-butene, the process according to the invention enables the residence times to be shortened, whereupon the undesired formation of higher oligomers is suppressed and in addition no noticeable isomerization of the valuable n-butene-1 into n-butene-2 takes place.

Furthermore, expensive separation operations to remove large excesses of methanol from $C_4$ hydrocarbons remaining after the preparation of methyl tert.-butyl ether are eliminated in the process according to the invention. According to the state of the art, such $C_4$ hydrocarbons must be freed from residual methanol by washing with water even for subsequent alkylation reactions.

The invention will be illustrated in more detail by the examples below, an apparatus according to FIG. 1 being used.

EXAMPLE 1

2,820 g of a $C_4$ stream from a steam cracker were fed first to the oligomerization and then to the etherification. The $C_4$ cut had the following composition: 2% by volume of i-butane, 8% by volume of n-butane, 47% by volume of i-butene, 27% by volume of n-butene-1 and 16% by volume of n-butene-2.

The oligomerization was carried out under a pressure of 17 bars and at a reaction temperature of 51° C.

The crosslinked polystyrene, containing sulphonic acid, Lewatit SPC 118 was employed as the catalyst. After 75% of the i-butene employed had been converted into diisobutene, 230 g of methanol were added. The space/hour velocity was 0.81 l of $C_4$ hydrocarbons/l of catalyst volume and hour.

The entire period of the experiment was 15 hours.

After the etherification, the product was introduced into a distillation column and the $C_4$ hydrocarbons were separated off from the remaining reaction mixture. 1,245 g of the $C_4$ raffinate were recovered, corresponding to 40.8% by weight of all the substances employed.

The analysis of the raffinate was as follows: 8.4% by weight of i-butane, 24.6% by weight of n-butane, 0.8% by weight of i-butene, 38.1% by weight of n-butene-1 and 28.1% by weight of n-butene-2.

1,805 g of product with the following composition were removed from the bottom of the column: <1% by weight of $C_4$ HC*, 50% by weight of $C_8$ HC, 19% by weight of $C_{12}$ HC, 2% by weight of $C_{16}$ HC, 27% by weight of MTBE and 2% by weight of methanol; bromine number (g of $Br_2$/100 ml)=100.

*=Hydrocarbons.

The proportion of reaction product was 59.2% by weight of the feed mixture.

The following values were determined for the engine data:

| RON | clear | 102.2 |
| --- | --- | --- |
| RON | 0.15 TEL/l | 103.2 |
| EON | clear | 83.6 |
| EON | 0.15 TEL/l | 85.7 |

After subsequent partial hydrogenation on a commercially available palladium catalyst, a bromine number of about 40 was established and the following engine data were obtained:

| RON | clear | 101.9 |
| --- | --- | --- |
| RON | 0.15 TEL/l | 102.9 |
| EON | clear | 87.3 |

| | | |
|---|---|---|
| -continued | | |
| EON | 0.15 TEL/l | 90.2 |

EXAMPLE 2

In a second experiment, an identical reactor system was filled with the acid ion exchanger, containing sulphonic acid groups, Amberlyst 15.

In contrast to Example 1, three times the amount of oligomer was circulated. The space/hour velocity could thereby be significantly increased.

In the present example, it was, based on the $C_4$ feed, 4.5 l of $C_4$ hydrocarbon/l of catalyst volume and hour.

The $C_4$ feed was again a $C_4$ stream from a steam cracker, after removal of butadiene, with the following composition: 2% by weight of i-butane, 8% by weight of n-butane, 47% by weight of i-butene, 27% by weight of n-butene-1 and 16% by weight of n-butene-2.

The oligomerization was carried out in a tube reactor at 51.2° C. A circulation stream, which corresponds to three times the amount of the $C_4$ hydrocarbon feed, was removed from an intermediate vessel after the oligomerization and before the etherification in order to dilute the feed product.

The etherification of the remaining i-butene in the reaction mixture was likewise carried out on Amberlyst 15.

The space/hour velocity, based on the $C_4$ feed, was 4.5. The pressure in the system was a constant 17 bars.

The experiment lasted 11 hours and 40 minutes.

Over this period, 3,190 g of $C_4$ hydrocarbons were introduced. 195 g of methanol were introduced in this period, after oligomerization of 76% of the i-butene. The reaction temperature in the etherification reactor was 63° C.

After the reaction, the product was passed to a column and the $C_4$ mixture was separated off, as the raffinate, from the remaining reaction product. The $C_4$ raffinate was found to be 1,430 g, and was thus 42.2% by weight of the total feed.

The analysis was as follows: 8.0% by weight of i-butane, 25.0% by weight of n-butane, 0.5% by weight of i-butene, 40.0% by weight of n-butene-1 and 26.5% by weight of n-butene-2.

1,955 g of a product with the following composition were removed from the bottom of the column: <1% by weight of $C_4$ HC, 57% by weight of $C_8$ HC, 14% by weight of $C_{12}$ HC, 2% by weight of $C_{16}$ HC, 26% by weight of MTBE and 1% by weight of methanol; bromine number (g of $Br_2$/100 ml)=100.

The proportion of the reaction product was 57.8% of the total feed. The following figures were determined for the engine data:

| | | |
|---|---|---|
| RON | clear | 102.2 |
| RON | 0.15 TEL/l | 103.1 |
| EON | clear | 85.4 |
| EON | 0.15 TEL/l | 86.8 |

EXAMPLE 3

In an existing system of five circulatory reactors, the reaction product was removed after the third reactor and the unreacted i-butene was etherified with methanol on Amberlyst 15. A hydrocarbon mixture, from the third circulatory reactor, with the following composition was employed: 44.5% by weight of $C_4$ HC, 35.2% by weight of $C_8$ HC, 18.9% by weight of $C_{12}$ HC and 1.4% by weight of $C_{16}$ HC.

The $C_4$ hydrocarbons still contained 9.5% of i-butene, which corresponds to an amount of 19.3% relative to the original feed. 185 g of methanol (1.1 times the molar amount, relative to i-butene) were added to 3 100 g of this product.

The etherification was carried out at a temperature of 63.5° C. under a pressure of 17 bars.

The space/hour velocity during the experiment was 4.1 l of $C_4$ hydrocarbon feed/l of catalyst volume and hour.

After the reaction, the $C_4$ hydrocarbons were separated off from the other reaction product in a distillation column.

The $C_4$ raffinate had the following composition: 4.4% by weight of i-butane, 16.3% by weight of n-butane, 0.6% by weight of i-butene, 38.9% by weight of n-butene-1 and 39.8% by weight of n-butene-2.

After separating off the $C_4$ hydrocarbons, the liquid reaction product had the following composition: <1% by weight of $C_4$ HC, 48.5% by weight of $C_8$ HC, 25.6% by weight of $C_{12}$ HC, 2.1% by weight of $C_{16}$ HC, 21.8% by weight of MTBE and 1% by weight of methanol.

The amount was 2,200 g and thus corresponded to 67.0% of the total feed.

What is claimed is:

1. A process for the preparation of a mixture consisting essentially of iso-butene oligomers and methyl tert.-butyl ether, which comprises:
   (a) contacting a mixture of straight chain branch butanes and butenes with an acid catalyst whereby to convert 50% to 90% by weight of the isobutenes contained therein and to diisobutylene and triisobutylene;
   (b) contacting the reaction mixture thus obtained with at least a molar amount of methanol, relative to any residual isobutene in the presence of an acid catalyst; and
   (c) separating off unreacted butanes and butenes from the reaction mixture.

2. A process according to claim 1, wherein a strongly acid ion exchanger is employed in at least step (a) or step (b).

3. A process according to claim 1, wherein a strongly acid ion exchanger is employed in both steps (a) and (b).

4. A process according to claim 2, wherein the ion exchanger contains sulphonic acid groups and is based upon a polystyrene cross-linked by divinyl benzene.

5. A process according to claim 1, wherein the stage (a) is carried out at a temperature of 20° to 120° C.

6. A process according to claim 1, wherein stages (a) and (b) are carried out in separate apparatuses and some of the reaction mixture from stage (a) is passed in circulation through the reaction for stage (a).

7. A process according to claim 1, wherein stage (b) is carried out at a temperature of 25° to 90° C.

8. A process according to claim 1, wherein stages (a) and (b) are carried out under a pressure such that the entire reaction mixture is in the liquid phase.

9. A process according to claim 1, wherein olefins which result from the process are partially or completely hydrogenated thereafter.

10. A fuel for a carburetor type engine consisting essentially of isobutene oligomers and methyl tert.-butyl ether, said fuel prepared by a process comprising:

(a) in a first step contacting a mixture of straight chain and branched butanes and butenes with an acid catalyst whereby to oligomerize 50% to 90% by weight of the isobutene contained therein;

contacting the reaction mixture from step (a) with at least a molar amount of methanol, relative to the residual isobutene, in the presence of an acid catalyst; and (c) separating off from the reaction mixture unreacted butanes and butenes.

11. A process according to claim 1, wherein the reaction mixture contacted according to step (b) with methanol contains diisobutylene and triisobutylene.

* * * * *

UNITED STATES PATENT AND TRADEMARK OFFICE
CERTIFICATE OF CORRECTION

PATENT NO. : 4,377,393

DATED : March 22, 1983

INVENTOR(S) : Bernhard Schleppingoff

It is certified that error appears in the above-identified patent and that said Letters Patent is hereby corrected as shown below:

Col. 8, line 18    Delete "butene" and insert --butane--

Col. 8, line 32    After "chain" insert --and--

Col. 9, line 6     Before "contacting" insert --(b)--

Signed and Sealed this

Seventh Day of June 1983

[SEAL]

Attest:

DONALD J. QUIGG

Attesting Officer    Acting Commissioner of Patents and Trademarks